United States Patent [19]

Boschi et al.

[11] Patent Number: 4,492,690

[45] Date of Patent: * Jan. 8, 1985

[54] PHOSPHORIC AND THIOPHOSPHORIC ESTERS OF 5(3)-HYDROXYPYRAZOLES EXERTING AN INSECTICIDAL ACTION

[75] Inventors: Pier M. Boschi, Piacenza; Franco Gozzo, S. Donato Milanese; Angelo Longoni, Milan, all of Italy

[73] Assignee: Montedison S.p.A., Milan, Italy

[*] Notice: The portion of the term of this patent subsequent to Jul. 10, 2001 has been disclaimed.

[21] Appl. No.: 524,229

[22] Filed: Aug. 18, 1983

Related U.S. Application Data

[63] Continuation of Ser. No. 426,881, Sep. 29, 1982, Pat. No. 4,459,294, which is a continuation of Ser. No. 182,680, Aug. 29, 1980, abandoned, which is a continuation of Ser. No. 129,724, Mar. 12, 1980, Pat. No. 4,256,902, which is a continuation-in-part of Ser. No. 971,548, Dec. 20, 1978, abandoned.

[30] Foreign Application Priority Data

Dec. 23, 1977 [IT] Italy ................................ 31190 A/77
Dec. 23, 1977 [IT] Italy ................................ 31191 A/77

[51] Int. Cl.³ ........................ A01N 57/16; C07D 9/65
[52] U.S. Cl. ..................................... 424/200; 548/116
[58] Field of Search ........................ 548/116; 424/200

[56] References Cited

U.S. PATENT DOCUMENTS 3,150,149 9/1964 Uhlenbroek et al. ............ 548/116 X
3,825,557 7/1974 Hoffmann et al. ............ 548/116 X
4,163,052 7/1979 Hofer et al. ........................ 424/200

*Primary Examiner*—Richard L. Raymond

*Attorney, Agent, or Firm*—Stevens, Davis, Miller & Mosher

[57] ABSTRACT

Phosphoric or thiophosphoric esters of 5(3)-hydroxypyrazoles are disclosed having the formula:

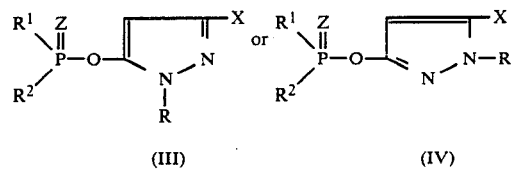

(III)            (IV)

wherein:
R=H; alkyl with 1–7 carbon atoms optionally substituted with halogens, CN, and carboalkoxy groups; phenyl optionally substituted; benzyl; alkenyl; or alkynyl;

X=halogen; —SR; —OR; —N(R)$_2$; or

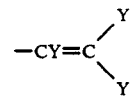

where Y is equal to or different from each other, and =H; C$_1$–C$_3$ alkyl; halogen; —SR; —OR; or —N(R)$_2$;

Z=S; or O; and

R$^1$ and R$^2$, equal to or different from each other, are: alkoxyls; alkyls; phenyls; or alkylthio- or alkylamino-groups.

These are useful as insecticides, acaricides and nematodacides.

7 Claims, No Drawings

PHOSPHORIC AND THIOPHOSPHORIC ESTERS OF 5(3)-HYDROXYPYRAZOLES EXERTING AN INSECTICIDAL ACTION

This is a continuation of application Ser. No. 426,881 filed Sept. 29, 1982 U.S. Pat. No. 4,459,294; in turn a continuation of Ser. No. 182,680, filed Mar. 12, 1980, now U.S. Pat. No. 4,256,802; in turn a continuation-in-part of Ser. No. 971,548 filed Dec. 20, 1978, abandoned.

The present invention relates to phosphoric acid thiophosphoric esters of 5(3)-hydroxypyrazoles substituted in 1 and 3(5) positions. More particularly, it relates to said compounds and their use as insecticides, acaricides and nematocides.

This invention relates also to 5(3)-hydroxypyrazoles having various substituents in a 3(5) position and, optionally, at one of the nitrogen atoms, as well as to general processes for their preparation.

The introduction of substituents into the 3 and 5 positions of the pyrazole ring presents some difficulties due to the particular reactivity of the pyrazole nucleus. In fact, for instance, pyrazoles substituted with halogen atoms in either position 3 or position 5 cannot be obtained by direct halogenation of the pyrazole nucleus, since the halogen atom is directed into position 4 (see Tetrahedron 33, 1977, pages 2069–2077).

In order to introduce the halogen atom into the 3 or 5 position it is necessary to substitute the hydroxyl group of the enolic form of the pyrazol-3-ones or pyrazol-5-ones by means of chlorinating agents (see Bulletin de la Societe Chimique de France, 1977, page 3727).

The compounds:

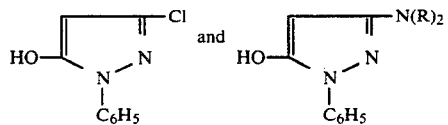

have been obtained respectively: the first one by treatment of 3,5-dihydroxy-1-phenyl-pyrazole with POCl$_3$ (see Berichte 31, 1898, page 3003); the second one was prepared from the former by substitution of the chlorine atom (see Chemical Abstracts 60, 15880a).

Recently a method was described for the preparation of pyrazoles substituted in either position 3 or position 5 with halogens or RO- groups; Aryl-O groups; RS- groups (see Tetrahedron 33 1977; pages 2069–2077).

Phosphoric esters of heterocyclic enolisable compounds amongst which are derivatives of 5- and 3-pyrazolone, have been described in British Pat. No. 713,278 of the Geigy Company including, amongst others, the diethyl-thiophosphoric ester of 3(5)-methyl-5(3)-hydroxypyrazole. Said compound has been marketed under the trademark "Pyrazothion".

We have now found, and these form one of the principal objects of this invention, 5(3)-hydroxy-pyrazoles not previously described and having the following general formulae:

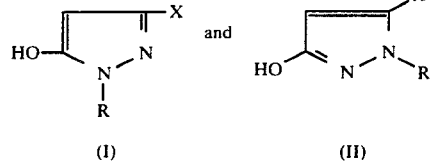

wherein
R=H; C$_1$-C$_7$ alkyl optionally substituted with CN groups, alkylcarboxylic groups, halogens, phenyl; phenyl substituted; benzyl; alkenyl; or alkynyl;
X=halogen; —SR; —OR; —N(R)$_2$, or

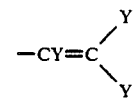

[Y, equal to or different from each other, are: H; C$_1$-C$_3$ alkyl; halogen; —SR; —OR; —N(R)$_2$] provided that, in the case in which in formula (I) X is a halogen or N(R)$_2$, the R-group bound to pyrazolic nitrogen is different from phenyl.

Further objects of this invention are the following general processes for obtaining 5(3)-hydroxy-pyrazoles optionally substituted at one of the nitrogen atoms (which in such a case, for nomenclature purposes, assumes position 1):

(a) When X=halogen; —SR; —OR; or —N(R)$_2$, a hydrazine R—NH—NH$_2$ (wherein R has the above indicated values), is made to react preferably in the form of a carbonyl derivative such as

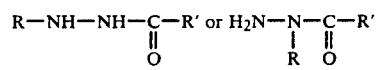

(wherein R′=NH$_2$, OR$^3$ and R$^3$, where R$^3$=alkyl), with the chloride of a β-chloro-β-X-acrylic acid.

The reaction product thus obtained is treated with an alkaline base, thereby effecting the cyclization and, at the same time, the elimination of the protective group

In this way the desired products are obtained in the form of alkaline salts, according to the following reactions:

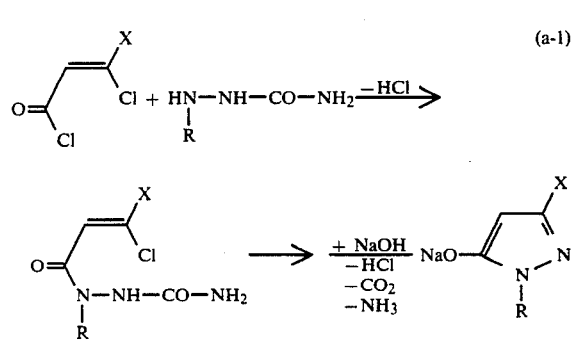

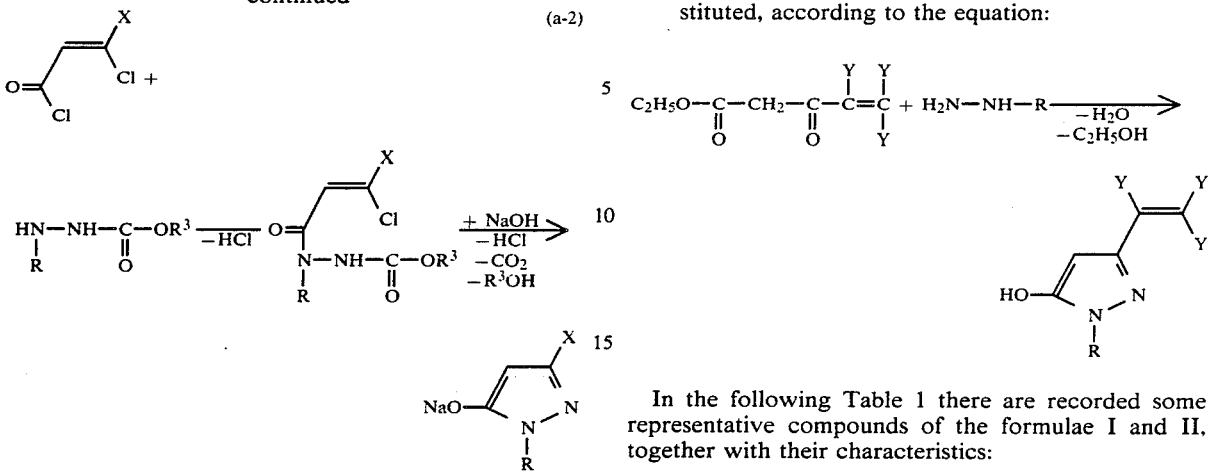

(Y)=CY₂, with a hydrazine optionally mono-substituted, according to the equation:

$$C_2H_5O-\underset{\underset{O}{\|}}{C}-CH_2-\underset{\underset{O}{\|}}{C}-\underset{\underset{Y}{|}}{C}=\overset{\overset{Y}{|}}{C} + H_2N-NH-R \xrightarrow[-C_2H_5OH]{-H_2O}$$

In the following Table 1 there are recorded some representative compounds of the formulae I and II, together with their characteristics:

TABLE I

3(5)-hydroxypyrazoles of general formulae I and II

| Compound | R | X | Method of preparation | Melting point (°C.) uncorrected | ELEMENTAL ANALYSIS | | | | | |
|---|---|---|---|---|---|---|---|---|---|---|
| | | | | | C % | | N (%) | | Cl % | |
| | | | | | Calc. | Found | Calc. | Found | Calc. | Found |
| A[1] | C₆H₅ | Cl | a-1 | 158–9 | 55.54 | 55.88 | 14.39 | 14.38 | 18.2 | 17.9 |
| B | C₂H₅ | Cl | a-2 | 145–7 | 40.95 | 41.1 | 19.11 | 19.0 | 24.13 | 23.9 |
| C[2] | i.C₃H₇ | Cl | a-2 | 138–40 | 44.87 | 44.93 | 17.44 | 17.87 | 5.65 | 5.66 |
| D | CH₂—CH₂—CN | Cl | a-2 | 166–7 | 42.00 | 42.34 | 24.49 | 24.49 | 20.57 | 20.03 |
| E[3] | CH₃ | CH=CCl₂ | b | 210 | 37.33 | 38.50 | 14.51 | 14.59 | 36.73 | 35.53 |
| F | C₆H₅ | CH=CCl₂ | b | 160–1 | 51.79 | 51.90 | 10.98 | 10.84 | 27.79 | 26.67 |
| G | CH₂—CH₂—CH | CH=CCl₂ | b | 179–80 | 41.59 | 41.1 | 18.1 | 17.9 | 30.35 | 29.46 |
| H | i.C₃H₇ | CH=CCl₂ | b | 167 | 43.45 | 43.1 | 12.67 | 12.4 | 30.55 | 32.3 |
| I | H | Cl | a-2 | 185–6 | 30.40 | 31.24 | 23.63 | 23.59 | 29.91 | 28.1– |
| J | H | CH=CCl₂ | b | 239–40 | 35.55 | 33.41 | 15.65 | 15.78 | 39.62 | 38.10 |
| K | CH₃ | Cl | a-1 | 186–8 | 36.25 | 36.30 | 21.13 | 21.07 | 26.75 | 26.11 |
| L | n.C₄H₉ | Cl | a-2 | 127–9 | 48.14 | 47.06 | 16.04 | 15.40 | 20.30 | 19.55 |
| M | i.C₄H₉ | Cl | a-2 | 176–7 | 48.14 | 49.08 | 16.04 | 16.19 | 20.30 | 19.90 |
| N | CH₂—C₆H₅ | Cl | a-2 | 202–3 | 57.57 | 57.90 | 13.43 | 12.75 | 16.98 | 16.28 |
| O | n.C₃H₇ | Cl | a-2 | 149–50 | 44.87 | 44.51 | 17.44 | 16.97 | 22.07 | 21.81 |
| P | c.C₄H₉ | Cl | a-1 | — | 48.14 | 48.79 | 16.04 | 14.52 | 20.30 | 18.37 |
| Q | i.C₃H₇ | Br | a-2 | 145–8 | 35.14 | 34.98 | 13.66 | 13.24 | 38.97 (Br) | 37.79 (Br) |
| R | s.C₄H₉ | Cl | a-2 | 140–2 | 48.14 | 49.10 | 16.04 | 15.95 | 20.30 | 19.54 |
| S | —CH—CH₃<br>   \|<br>CH₂—CH(CH₃)₂ | Cl | a-2 | 133–4 | 53.33 | 53.16 | 13.82 | 13.70 | 17.50 | 17.25 |
| T | p.NO₂—C₆H₄ | Cl | (4) | 261–3 | 45.11 | 45.53 | 17.54 | 16.81 | 14.79 | 14.00 |

Notes to Table 1
[1]NMR (δ, ppm) [s = singlet, d = doublet, h = heptaplet, m = multiplet]
7.1–7.8 (m, aromatic protons)
5.6 (s, pyrazolic CH)
9.5 (OH)
[2]NMR (δ, ppm)
4.4 [h, CH(CH₃)₂]
1.3 [d, CH(CH₃)₂]
5.35 (s, pyrazolic CH)
[3]NMR (δ, ppm)
5.8 (s, CH = CCl₂)
6.8 (s, pyrazolic CH)
3.4 (OH)
[4]Compound II T has been prepared according to the following scheme:

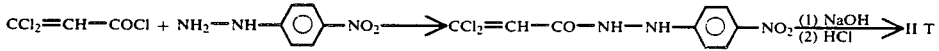

By acidification of the alkaline salts the desired 5-hydroxy (or 3-hydroxy) pyrazoles are obtained.

(b) When X is a vinyl group optionally substituted, the synthesis consists in reacting an ethyl-acryloacetate, of formula C₂H₅O—CO—CH₂—CO—C-

The processes for the preparation of 3(5)-hydroxypyrazoles hereinabove described are of a perfectly general character and are not restricted to the preparation of the compounds containing the particular substitutions of formulae I and II.

Moreover we have found, and so they too are an important object of this invention, phosphoric and thiophosphoric esters of 5(3)-hydroxypyrazoles substituted in position 3(5) of general formulae

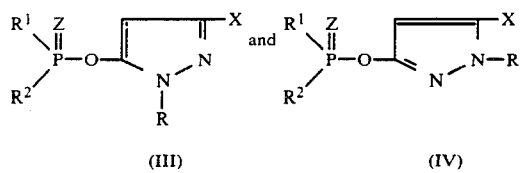

(III)                    (IV)

wherein:
R = H; $C_1$-$C_7$ alkyl optionally substituted with CN groups, alkylcarboxylic groups, or halogens; phenyl optionally substituted; benzyl; alkenyl; and alkynyl;
X = halogen; —SR; —OR; —N(R)$_2$ or

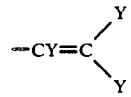

[Y, equal to or different from each other, are: H; $C_1$-$C_3$ alkyl; halogen; —SR; —OR; or —N(R)$_2$];
Z = S; O; and
$R^1$ & $R^2$, equal to or different from each other, = alkoxyl, alkyl, phenyl, alkylthio or alkylamino-groups.

These compounds have a very high activity against numerous noxious insects, acari and nematoda. Their activity is superior to that of known chemically related compounds such as for instance "Pyrazothion", and, in some cases, the latter does not shown activity (see Table III).

Compounds of the general formula III and IV may be obtained by reacting a (thio)phosphoric acid halide with an alkaline salt of hydroxypyrazole, (see Example 11 below) according to the following scheme:

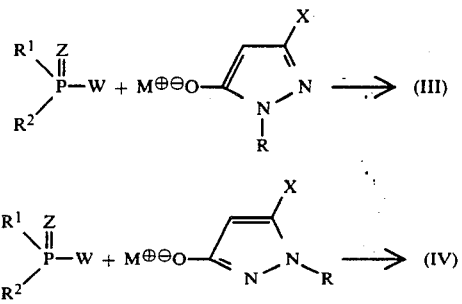

(wherein R, $R^1$, $R^2$, X and Z have the meanings reported for general formulae III and IV, W = halogen and $M^+$ = alkaline metal cation).

The thiophosphoric esters of 5(3)-hydroxypyrazoles reported below in Table 2 have been prepared according to the above-described method.

TABLE 2

Thiophosphoric ester of 5(3)-hydroxypyrazoles of formulae III and IV (Z = S)

| | | | | | | ELEMENTAL ANAYLSIS | | | |
|---|---|---|---|---|---|---|---|---|---|
| | | | | | | Cl (%) | | S (%) | |
| Compound | Formula | R | $R^1$ | $R^2$ | X | calc. | found | calc. | found |
| 1 | III | $C_6H_5$ | $CH_3O$ | $CH_3O$ | Cl | 11.13 | 13.38 | 10.06 | 9.07 |
| 2 | III | $C_6H_5$ | $C_2H_5O$ | $C_2H_5O$ | Cl | 10.22 | 10.17 | 9.25 | 8.62 |
| 3 | III | $C_2H_5$ | $C_2H_5O$ | $C_2H_5O$ | Cl | 11.87 | 11.82 | 10.73 | 11.10 |
| 4 | III | i.$C_3H_7$ | $CH_3O$ | $CH_3O$ | Cl | 12.45 | 11.69 | 10.26 | 10.06 |
| 5 | III | i.$C_3H_7$ | $C_2H_5O$ | $C_2H_5O$ | Cl | 11.33 | 10.76 | 10.25 | 9.90 |
| 6 | III | $CH_3$ | $C_2H_5O$ | $C_2H_5O$ | —CH=CCl$_2$ | 20.57 | 19.96 | 9.29 | 8.25 |
| 7 | III | $CH_2$—$CH_2$—CN | $C_2H_5O$ | $C_2H_5O$ | Cl | 10.95 | 10.18 | 9.90 | 9.59 |
| 8 | III | $C_6H_5$ | $C_2H_5O$ | $C_2H_5O$ | CH=CCl$_2$ | 17.71 | 16.5 | 7.87 | 6.93 |
| 9 | III | $CH_2$—$CH_2$—CN | $C_2H_5O$ | $C_2H_5O$ | CH=CCl$_2$ | 18.22 | 17.65 | 8.34 | 7.39 |
| 10 | III | i.$C_3H_7$ | $C_2H_5O$ | $C_2H_5O$ | CH=CCl$_2$ | 19.00 | 18.1 | 8.68 | 7.9 |
| 11 | III | H | $C_2H_5O$ | $C_2H_5O$ | Cl | 13.10 | 12.42 | 11.85 | 11.38 |
| 12 | III | H | $C_2H_5O$ | $C_2H_5O$ | CH=CCl$_2$ | 21.41 | 20.69 | 9.68 | 9.03 |
| 13 | III | $CH_3$ | $C_2H_5O$ | $C_2H_5O$ | Cl | 12.45 | 12.00 | 11.26 | 10.81 |
| 14 | III | $CH_3$ | $CH_3O$ | $CH_3O$ | Cl | 13.81 | 13.39 | 12.49 | 12.49 |
| 15 | III | n.$C_4H_9$ | $C_2H_5O$ | $C_2H_5O$ | Cl | 10.85 | 10.44 | 9.81 | 9.22 |
| 16 | III | n.$C_4H_9$ | $CH_3O$ | $CH_3O$ | Cl | 11.86 | 11.64 | 10.73 | 10.42 |
| 17 | III | $CH_3$ | n.$C_3H_7O$ | n.$C_3H_7O$ | Cl | 11.33 | 10.53 | 10.25 | 9.76 |
| 18 | III | $CH_2$—$CH_2$CN | $CH_3O$ | $CH_3O$ | Cl | 11.99 | 12.03 | 10.85 | 10.52 |
| 19 | III | $CH_2$—$CH_2$—CN | H.$C_3H_7O$ | n.$C_3H_7O$ | Cl | 9.79 | 9.96 | 8.86 | 8.89 |
| 20 | III | $CH_3$ | $C_2H_5O$ | $C_6H_5$ | Cl | 11.19 | 10.84 | 10.12 | 10.36 |
| 21 | III | $C_2H_5$ | $CH_3O$ | $CH_3O$ | Cl | 13.10 | 12.99 | 11.84 | 11.76 |
| 22 | III | $CH_3$ | $C_2H_5O$ | $C_6H_5$ | CH=CCl$_2$ | 18.74 | 18.11 | 8.47 | 8.36 |
| 23 | III | $CH_3$ | $CH_3O$ | $C_2H_5O$ | Cl | 13.10 | 13.08 | 11.84 | 11.27 |
| 24 | III | $C_2H_5$ | $CH_3O$ | $C_2H_5O$ | Cl | 12.45 | 12.54 | 11.25 | 9.85 |
| 25 | III | $CH_2$—CH($CH_3$)$_2$ | $C_2H_5O$ | $C_2H_5O$ | Cl | 10.84 | 10.67 | 9.81 | 8.80 |
| 26 | III | $CH_2$—CH($CH_3$)$_2$ | $CH_3O$ | $CH_3O$ | Cl | 11.86 | 11.62 | 10.73 | 10.80 |
| 27 | III | $CH_3$ | $C_2H_5O$ | N($CH_3$)$_2$ | Cl | 12.50 | 12.04 | 11.30 | 11.18 |
| 28 | III | i.$C_3H_7$ | $CH_3O$ | $C_2H_5O$ | Cl | 11.86 | 11.63 | 10.73 | 9.80 |
| 29 | III | $CH_2$—$C_6H_5$ | $C_2H_5O$ | $C_2H_5O$ | Cl | 9.82 | 9.85 | 8.88 | 8.67 |
| 30 | III | n.$C_3H_7$ | $C_2H_5O$ | $C_2H_5O$ | Cl | 11.33 | 11.10 | 10.25 | 10.07 |
| 31 | III | n.$C_3H_7$ | $CH_3O$ | $CH_3O$ | Cl | 12.45 | 12.29 | 11.25 | 10.72 |
| 32 | III | CH($CH_3$)—$C_2H_5$ | $CH_3O$ | $CH_3O$ | Cl | 11.86 | 11.54 | 10.73 | 10.80 |
| 33 | III | CH($CH_3$)—$C_2H_5$ | $C_2H_5O$ | $C_2H_5O$ | Cl | 10.84 | 10.52 | 9.81 | 9.83 |
| 34 | III | CH($CH_3$)—$C_2H_5$ | $CH_3O$ | $C_2H_5O$ | Cl | 11.33 | 11.02 | 10.25 | 10.18 |
| 35 | III | $CH_3$ | $C_2H_5O$ | N($CH_3$)$_2$ | CH=CCl$_2$ | 20.54 | 20.18 | 9.29 | 9.15 |
| 36 | III | H | $CH_3O$ | $C_2H_5O$ | Cl | 13.82 | 13.53 | 12.50 | 12.42 |
| 37 | III | $C_6H_5$ | $CH_3O$ | $C_2H_5O$ | Cl | 10.65 | 10.49 | 9.63 | 9.27 |
| 38 | III | $CH_2$—$CH_2$—CN | $CH_3O$ | $C_2H_5O$ | Cl | 11.44 | 10.85 | 10.35 | 9.31 |
| 39 | III | C($CH_3$)$_3$ | $C_2H_5O$ | $C_2H_5O$ | Cl | 10.84 | 10.50 | 9.81 | 9.89 |

TABLE 2-continued

Thiophosphoric ester of 5(3)-hydroxypyrazoles of formulae III and IV (Z = S)

| Compound | Formula | R | $R^1$ | $R^2$ | X | Cl (%) calc. | Cl (%) found | S (%) calc. | S (%) found |
|---|---|---|---|---|---|---|---|---|---|
| 40 | III | $CH_2-CH_2-CN$ | $CH_3O$ | $C_2H_5O$ | $CH=CCl_2$ | 19.15 | 18.70 | 8.66 | 8.35 |
| 41 | III | $i.C_3H_7$ | $C_2H_5O$ | $C_2H_5O$ | Br | 22.37 (Br %) | 22.63 (Br %) | 8.98 | 8.42 |
| 42 | III | $CH(CH_3)-CH_2-CH(CH_3)_2$ | $CH_3O$ | $CH_3O$ | Cl | 10.85 | 10.73 | 9.81 | 9.55 |
| 43 | III | $CH(CH_3)-CH_2-CH(CH_3)_2$ | $C_2H_5O$ | $C_2H_5O$ | Cl | 9.99 | 9.87 | 9.04 | 8.75 |
| 44 | III | $i.C_3H_7$ | $C_2H_5O$ | $C_2H_5$ | Cl | 11.94 | 11.55 | 10.81 | 10.66 |
| 45 | III | $CH_3$ | $C_2H_5O$ | $C_2H_5$ | Cl | 13.19 | 12.71 | 11.94 | 11.54 |
| 46 | III | $C_6H_5$ | $C_2H_5O$ | $C_2H_5$ | Cl | 10.71 | 10.44 | 9.69 | 8.86 |
| 47 | III | H | $C_2H_5O$ | $C_2H_5$ | Cl | 13.92 | 13.71 | 12.59 | 12.48 |
| 48 | III | $i C_3H_7$ | $C_2H_5O$ | $NH-CH(CH_3)_2$ | Cl | 10.88 | 10.33 | 9.51 | 9.13 |
| 49 | III | $CH_3$ | $C_2H_5O$ | $NH-CH(CH_3)_2$ | Cl | 11.91 | 11.90 | 10.77 | 10.23 |
| 50 | IV | $p.NO_2-C_6H_5$ | $CH_3O$ | $CH_3O$ | Cl | 9.76 | 9.29 | 8.80 | 8.46 |
| 51 | IV | $p.NO_2-C_6H_5$ | $CH_3O$ | $C_2H_5O$ | Cl | 9.39 | 9.06 | 8.49 | 7.88 |
| 52 | IV | $p.NO_2-C_6H_4$ | $C_2H_5O$ | $C_2H_5O$ | Cl | 9.05 | 6.88 | 8.19 | 7.51 |

The compounds of general formulae III and IV exert a considerable activity against insects such as lepitoptera, diptera, coleoptera, etc.; acaria; and nematoda.

The pesticidal activity, verified by the methods described below in Example 12, is recorded below in the following Table 3 in comparison with that of "Pyrazothion".

As appears quite clearly from the data reported in Table 3, the compounds of general formula III and IV display an activity superior to that of the witness compound on Blatta and Macrosiphum and are unexpectedly active against Spodoptera, Culex, Musca, Leptinotarsa, Meloidogine incognita on which the witness compound proves to be ineffective.

TABLE 3

Activity of the compounds of the invention against insects, acari and nematoda at the indicated doses, expressed as percentage of reduction of the infestation.

| Compound see Table 2 | Pieris B (0.1°/oo) | Spocoptera L (0.1°/oo) | Culex larvae (0.2 ppm) | Culex ad. (0.2 g/m²) | Musca d. (0.5 γ/ins) | Leptinot D. (0.1°/oo) | Macrosipn. E. (0.01°/oo) | Tetran U. (0.01°/oo) | Meloidog. I. (20 ppm) | Blatta C (0.1 g/m) |
|---|---|---|---|---|---|---|---|---|---|---|
| 1 III | 100 | 100 | 100 | 100 | 100 | 100 | 90 | 60 | 80 | 100 |
| 2 III | 100 | 100 | 100 | 100 | 100 | 97 | 40 | — | — | 100 |
| 3 III | 100 | 82 | 100 | 100 | 100 | 100 | 98 | 100 | 96 | 100 |
| 4 III | — | 80 | 100 | 100 | 100 | 100 | 94 | 20 | — | 100 |
| 5 III | 100 | 60 | 100 | 100 | 100 | 100 | 100 | 100 | 90 | 100 |
| 6 III | 100 | 100 | 100 | 76 | 100 | 100 | 100 | 100 | 95 | 100 |
| 7 III | 100 | 100 | 100 | 70 | 100 | 100 | 100 | 100 | 100 | 100 |
| 9 III | 100 | 100 | 100 | 0 | 100 | 100 | 85 | 85 | — | 100 |
| 11 III | 100 | 65 | 100 | 90 | 5 | 70 | 100 | 100 | — | 100 |
| 13 III | 100 | 100 | 100 | 100 | 100 | 100 | 99 | 100 | 100 | 100 |
| 14 III | 100 | 82 | 100 | 100 | 100 | 37 | 96 | 100 | 41 | 100 |
| 21 III | 100 | 70 | 100 | 100 | 100 | 100 | 100 | 100 | 100 | 100 |
| 23 III | 100 | 100 | 100 | 100 | 100 | 100 | 92 | 100 | 100 | 100 |
| 24 III | 100 | 90 | 100 | 100 | 100 | 100 | 96 | 100 | 62 | 100 |
| 29 III | 100 | 100 | 100 | 5 | 100 | 100 | 60 | 100 | 59 | 100 |
| 37 III | 100 | 100 | 100 | 100 | 100 | 100 | 48 | 0 | 47 | 100 |
| 44 III | 100 | 55 | 100 | 100 | 100 | 100 | 91 | 100 | — | 100 |
| 49 III | 100 | 15 | 100 | 100 | 100 | 100 | 81 | 63 | — | 100 |
| 52 IV | 100 | 95 | 100 | 0 | 100 | 37 | 54 | 96 | 96 | 100 |
| 51 IV | 100 | 100 | 100 | 0 | 100 | 85 | 51 | 94 | 82 | — |
| "Pyrazothion" (Reference compound) | 70 | 0 | 0 | 0 | 0 | 0 | 60 | 90 | 0 | 20 |

The compounds of general formula III and IV display, moreover, another unexpected characteristic favorable for their use as pesticides. In fact they are endowed, in general, with a relatively low toxicity with respect to mammals, their toxicity, as appears from Table 4, being in most cases considerably lower than that of "Pyrazothion".

TABLE 4

| | Toxicity by os on rats (mg/Kg) | | |
|---|---|---|---|
| Compound n° | LD 50 | Compound n° | LD 50 |
| 1 | 400 | 13 | 25 |
| 2 | 33 | 14 | 560 |
| 4 | 1100 | 23 | 487 |
| 5 | 22 | 37 | 320 |
| 6 | 175 | "Pyrazothion" | 36 |
| 11 | 70 | | |

The compounds of this invention may be formulated into readily useable compositions according to the usual techniques: e.g., in powders, wettable powders, solutions, emulsions or suspensions.

In order still better to illustrate the inventive idea, a following series of examples is given:

EXAMPLE 1

Preparation of 1-phenyl-3-chloro-5-hydroxypyrazole (method a-1)

To a suspension of 7 g of 1-phenylsemicarbazide in 100 ml of acetonitrile, cooled down to 0°-5° C., were added 7.4 g of $\beta,\beta$-dichloroacryloyl chloride, under stirring. The addition having been completed, the reaction mixture was stirred at 5° C. for 30 minutes and then at room temperature for 1 (one) hour. The solid that separated was collected by decanting and by filtration, then was washed with diethylether, thus obtaining 8 g of 1-($\beta,\beta$-dichloroacryloyl)-1-phenyl-semicarbazide, in accordance with the elemental analysis and the I.R. and N.M.R. spectra.

By evaporation to dryness of the mother liquors of the reaction, a solid residue was collected which, after washing with diethylether, yielded a further 3 g of the same product.

To a 10% aqueous solution of NaOH (110 g), kept under stirring at a temperature between 55° and 60° C., were added in small portions 5.5 g of 1-($\beta,\beta$-dichloroacryloyl)-1-phenyl semicarbazide.

Upon completion of the addition, the solution was maintained at 60° C. for 10 minutes, after which it was allowed to cool down, then diluted with 50 ml of H$_2$O, and finally poured dropwise into a slight excess of diluted solution of HCl. In this way a precipitate was formed.

The mixture thus obtained was extracted with diethylether (50 ml×3) and the extract, after evaporation of the solvent, yielded 4 g of 1-phenyl-3-chloro-5-hydroxypyrazole.

The mass, NMR, and IR spectra, as well as the elemental analysis, were consistent with the assigned structure.

EXAMPLE 2

Preparation of 1-isopropyl-3-chloro-5-hydroxypyrazole (method a-2)

To a chloroforme solution of 5 g of 1-isopropyl-2-carboethoxyhydrazine were added 3 g of triethylamine and then, dropwise and under stirring, 5.5 g of $\beta,\beta$-dichloroacryloylchloride, while maintaining the temperature between 0° and −5° C.

After the addition was completed, the chloroformic solution was washed with a diluted aqueous solution of hydrochloric acid, dehydrated with Na$_2$SO$_4$, and finally the solvent was evaporated, thereby obtaining 8.1 g of 1-($\beta,\beta$-dichloro-acryloyl)-1-isopropyl-2-carbethoxyhydrazine whose elemental analysis was in agreement with the assigned structure.

5 g of this intermediate were added to a solution of 5 g of NaOH in 100 ml of H$_2$O, maintained under stirring at 60° C. As soon as the solution became clear, it was cooled down to room temperature and then acidified with 10 ml of concentrated HCl. The solid that separated was extracted with chloroform (50 ml×3). After evaporation of the solvent, there were obtained 2.7 g of 1-isopropyl-3-chloro-5-hydroxypyrazole (M.P. 138°-140° C.).

The mass, NMR, and IR spectra, as well as the elemental analysis, were consistent with the assigned structure.

EXAMPLES 3-5 (method a-2)

By the same process as that described above in Example 2, there were prepared, starting from the following hydrazine derivatives, the compounds listed hereunder:

| | | |
|---|---|---|
| C$_2$H$_5$—NH—NH—COOC$_2$H$_5$ | → | 1-ethyl-3-chloro-5-hydroxypyrazole |
| H$_2$N—NH—COOC$_2$H$_5$ | → | 3(or 5)-chloro-5(or 3)-hydroxypyrazole |
| NC—CH$_2$—CH$_2$—NH—NH—COO$_2$H$_5$ | → | 1-(2-cyanoethyl)-3-chloro-5-hydroxypyrazole |

EXAMPLE 6

Preparation of 1-methyl-3-($\beta,\beta$-dichlorovinyl)-5-hydroxypyrazole (Method b)

To 2.1 g of ethyl $\beta,\beta$-dichloroacryloylacetate in 10 ml of acetic acid were added, under constant stirring, 0.46 g of methylhydrazine. This reaction mixture was maintained for 1 (one hour) at 75° C. and then for 1 (one) hour at 110° C. Thereupon the reaction mixture was allowed to cool down, whereupon it was then diluted with 60 ml of water. The solid that gradually precipitated was extracted with ethyl acetate.

This extract was then washed with an aqueous solution of NaHCO$_3$ and then the solvent was evaporated, thereby yielding 1.5 g of 1-methyl-3-($\beta,\beta$-dichlorovinyl)-5-hydropyrazole (m.p.=210° C., after washing with diethylether).

EXAMPLES 7-10 (method b)

Following the same procedure as that described above in Example 6, and starting from the following hydrazines, there were prepared the compounds listed hereunder:

| | | |
|---|---|---|
| H$_2$N—NH$_2$ | → | 3-(or 5)-($\beta,\beta$-dichlorovinyl)-5-(or 3) hydroxypyrazole |
| i-C$_3$H$_7$—NH—NH$_2$ | → | 1-isopropyl-3-($\beta,\beta$-dichlorovinyl-5-hydroxypyrazole |
| NC—CH$_2$—CH$_2$—NH—NH$_2$ | → | 1-(2-cyanoethyl)-3-($\beta,\beta$-dichlorovinyl)-5-hydroxypyrazole |
| C$_6$H$_5$—NH—NH$_2$ | → | 1-phenyl-3-($\beta,\beta$-dichlorovinyl)-5-hydroxypyrazole |

EXAMPLE 11

Preparation of O,O-dimethyl-0-(1-phenyl-3-chloropyrazol-5-yl)thiophosphate

To 5 g of 1-phenyl-3-chloro-5-hydroxypyrazole in 120 ml of acetone were added 5.3 g of $K_2CO_3$ and 4.12 g of O,O-dimethylthiophosphorylchloride. This reaction mixture was kept under stirring for 4 hours and was then filtered in order to remove the inorganic salts.

After evaporation of the solvent, there were obtained 8 g of O,O-dimethyl-0-(1-phenyl-3-chloropyrazol-5-yl)thiophosphate in the form of an oil (compound 1, Table 2).

In the same way all the other compounds reported in Table 2 were prepared.

EXAMPLE 12

Biological activity on *Macrosiphum euphorbiae* (aphides)

Small potato plants grown in pots were infested with adult female aphides and, after several hours, were sprinkled with an aqueous dispersion of the products under examination.

The percentage death rate was determined 24 hours after treatment (untreated plants=0).

Biological activity on *Pieris brassicae* (Lepitoptera)

Cut cauliflower leaves were sprinkled with an aqueous dispersion of the products under examination. After drying, the leaves were infested with 5-day old larvae. The percentage death rate of the larvae (untreated leaves=0) was determined 48 hours after treatment.

Biological activity on *Leptinotarsa decemlineata* (Coleoptera)

Small, pot-grown potato-plants were infested with 4-day old larvae, and then were sprinkled with an aqueous dispersion of the products under examination. The percentage death rate (untreated plants=0) was determined 48 hours after treatment.

Biological activity on *Culex pipiens* (diptera) larvae

Into glasses containing an aqueous dispersion of the products under examination, were introduced third and fourth age mosquito larvae. The percentage death rate of the larvae (glasses containing pure water=0) was determined 24 hours after treatment.

Biological activity on *Tetranychus urticae* (Acari) adults

Small bean leaf discs were infected with adult acari and were then sprinkled with an aqueous dispersion of the products under examination. The percentage of mortality was determined 24 hours after the treatment (untreated discs, mortality=0).

Biological activity on *Spodoptera littoralis* (Lepidoptera)

Cut tobacco leaves were sprinkled with an aqueous dispersion of the products under examination. After drying, the leaves were infested with 5-days old larvae. The percentage mortality of the larvae was determined 48 hours after treatment (untreated leaves, mortality=0).

Biological activity on *Meloidogyne ingognita* (Nematoda)

Aliquot parts of a 1:1 mixture of field soil and sand, infested by Nematoda larvae and eggs, were treated by uniformly mixing same with an aqueous dispersion of the products under examination. The soil was then distributed into plastic pots, and after 5 days into each pot there were transplanted 5 tomato plants about 20 cm high. The survey of the results was carried out 21 days after the transplanting, by observing the roots of the plants extracted from the soil in order to ascertain the degree of infestation by counting the galls that have formed on them. The nematocide activity was expressed as a percentage of reduction of the infestation with respect to the witness plant (small plants transplanted into untreated soil, activity=0).

Biological activity on *Blatta orientalis* (Ortoptera)

The bottom and side walls of glass beakers were treated uniformly with an acetonic solution of the products under examination. After evaporation of the solvent in each beaker, into the same were then introduced ten, 80–100 days old neanides, whereafter they were closed with a lid of metal netting. After 24 hours from the beginning of the treatment, the insects were transferred into untreated glass beakers, and suitably nourished. The percentage mortality (untreated insects=0) was determined 48 hours after the start of the treatment.

Biological activity on *Musca domestica* (Diptera)

4-days old adults were treated, by topical application by microsyringe, with an acetonic solution of the products under examination.

The mortality percentage (insects treated with acetone only=0) was determined 24 hours after the treatment.

Biological activity on *Culex pipiens* (Diptera): adults

Whatman n°1 paper rectangles were treated uniformly with an acetonic solution of the products under examination. After evaporation of the solvent, each treated paper rectangle was used to line the inside wall of a perspex cylinder (model OMS). The paper-lined perspex cylinder was then closed with a net after having introduced into it 2–3 days old adult females. After one hour from the start of the contact, the insects were transferred into a similar cylinder likewise lined with untreated paper, and were fed with a sugary solution.

The mortality percentage (untreated insects=0) was determined 24 hours after the beginning of the treatment.

What is claimed is:

1. A thiophosphoric ester of a 5-hydroxypyrazole, having the formula

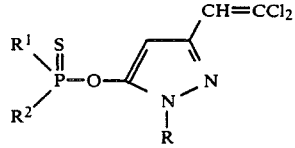

wherein:
R=H, alkyl with from 1 to 7 carbon atoms, optionally substituted with the CN group, or phenyl; and
$R^1$ and $R^2$, equal to or different from each other, =O-alkyl.

2. O,O-diethylthiophosphoric ester of 1-methyl-3-($\beta,\beta$-dichlorovinyl)-5-hydroxypyrazole.

3. O,O-diethylthiophosphoric ester of 1-isopropyl-3-($\beta,\beta$-dichlorovinyl)-5-hydroxypyrazole.

4. O,O-diethylthiophosphoric ester of 1-($\beta$-cyanoethyl)-3-($\beta,\beta$-dichlorovinyl)-5-hydroxypyrazole.

5. O,O-diethylthiophosphoric ester of 1-phenyl-3-($\beta,\beta$-dichlorovinyl)-5-hydroxypyrazole.

6. A method for fighting infestations of insects, acari and nematoda, said method consisting in spreading onto the "habitat" of the parasite an effective amount of a compound as defined in claim 1.

7. A composition for fighting infestations of insects, acari and nematoda, characterized in that such compositions contain as active ingredient a compound as defined in claim 1, in quantities ranging from 0.1% upwards by weight together with an inert carrier.

* * * * *